US00PP09704P

United States Patent [19]

Van Rijn

[11] Patent Number: Plant 9,704

[45] Date of Patent: Nov. 19, 1996

[54] ANTHURIUM PLANT NAMED 'ELISABETH'

[75] Inventor: Magdalena J. M. Van Rijn, Schipluiden, Netherlands

[73] Assignee: Van Rijn Plants, Am Schipluiden, Netherlands

[21] Appl. No.: 510,566

[22] Filed: Aug. 2, 1995

[51] Int. Cl.[6] ..... A01H 5/00

[52] U.S. Cl. ..... Plt./88.1

[58] Field of Search ..... Plt./88.1

*Primary Examiner*—James R. Feyrer
*Attorney, Agent, or Firm*—Foley & Lardner

[57] ABSTRACT

An *Anthurum* plant named 'Elisabeth' having ovate leaves. The spathe has oval lobes and is held above the leaves. The spadix color is white-cream at the base and the distal portion is yellow with a flush of green. 'Elisabeth' grows rapidly and has a medium growth habit.

3 Drawing Sheets

The present invention comprises a new and distinct cultivar of *Anthurium,* botanically known as *Anthurium andreanum* and referred to by the cultivar name 'Elisabeth'.

The new cultivar is a product of a planned breeding program, and was originated from a cross made during such a program in Schipluiden, Netherlands, on Jul. 10, 1990. The female or seed parent was cultivar 'Jolanda.' The male, or pollen parent was the cultivar 'Lady Janes.'

'Elisabeth' was discovered and selected Feb. 23, 1992 as a flowering plant within the progeny of the stated cross by Magdalena J. M. Van Rijn in a controlled environment in Nursery Schipluiden. Subsequent asexual reproduction by tissue culture at the same location has demonstrated that the combination of characteristics as herein disclosed for the new cultivar are firmly fixed and are retained through successive generations of asexual reproduction.

The following traits have been repeatedly observed and in combination distinguish 'Elisabeth' as a new and distinct cultivar.

1. Quick grower producing many flowers in a short time.
2. Flowers continually.
3. Large plant with medium green leaves and strong branching.
4. Large leave with acute tips. Leaves are on long petioles and the petioles are light green.
5. The peduncles are long and have a light green color.
6. The spathe size is large with overlapping lobes and the shape is broad ovate. The distal part of the spathe is rounded and the tip is acuminate.
7. The main color of the upper surface of the leaves is R.H.S. 38 A-B.
8. The spadix length is medium and its longitudinal axis is weakly recurved. The tapering toward the top is medium to strong. The main color of the basal portion of the spadix is white and the main color of the distal portion is yellow with a flush of green.

The following observations, measurements and values describe plants grown in Schipluiden, the Netherlands under greenhouse conditions which closely approximate those generally used in horticultural practice. Color references are made to The Royal Horticultural Society Colour Chart (R.H.S.), except where general color terms of ordinary significance are used.

The color values were determined between 13:30 h and 14:00 h on Apr. 7, 1995 under natural light at 's-Gravenzande, the Netherlands. The light intensity was 1210 J/m$^2$.

The following color photographic drawings are of 'Elisabeth' grown in a 19 cm pot.

Sheet 1 is a top prespective of the plant.

Sheet 2 shows the spathe and,

Sheet 3 the spadix of 'Elisabeth.'

Classification:
- *Botanical.*—*Anthurium andreanum,* cv. 'Elisabeth'.
- *Commercial.*—'Elisabeth'.

Parentage:
- *Male parent.*—'Lady Jane'.
- *Female parent.*—'Jolanda'.

Propagation: Tissue culture.
- *Growth habit.*—Normal growth.

Plant: At maturity the plant measures 35–40 cm in height without flowers and 45–50 cm in height with flowers. At maturity the plant measures approximately 50 cm in diameter.

Leaves:
- *Form.*—Ovate, acute tip, position of the lobes is free.
- *Size.*—The leaves are large and are almost twice as long as wide.
- *Texture.*—Medium blistering.
- *Veins.*—Veins appear to be slightly lighter green than the leaves. Veins are clearly visible and are most apparent at the base becoming thinner towards the leaf margin.
- *Color.*—Upper side: R.H.S. 137 A, lower side: R.H.S. 143 C.

Flowers:
- Buds.—Color is lighter than the opened flower with veins that are light green at the tip.

Spathe:
- *Size.*—Large, approximately 9 cm long×12 cm wide.
- *Color.*Upper side: approximately R.H.S. 38 A-B. Lower side: approximately R.H.S. 38 C-D. Arrangement: Spathe is held above the leaves. Shape: Broad ovate, the position of the lobes is overlapping, their distal part is rounded and the tip is acuminate, blistering is medium to strong. Flowering time: in winter 6 weeks, in summer 3 months.

Reproductive organs:
- *Spadix.*—Length 7–8 cm; diameter 7–8 mm; cross-section is elliptic, longitudinal axis is weakly recurved, tapering at distal end is medium to strong; the color of the basal portion is white-cream and the main color of the distal portion is yellow with a flush of green.
- *Stamen.*—Protogynous. Color equal to that of spadix.
- *Anthers and filaments.*—No filaments, anthers are sitting directly onto the spadix.
- *Pollen.*—Color white cream.

Roots: Thick roots in white yellow color.

Disease Resistance: Unknown.

GENERAL OBSERVATIONS

The *Anthurium* plant name 'Elisabeth' is a plant with ovate leaves. The spathe has oval lobes and is held above the leaves. The spadix color is white-cream at the base and the dital portion is with a flush of green. 'Elisabeth' grows rapidly and has a medium growth habit.

| | Comparative Varieties | |
|---|---|---|
| Characteristic | Cultivar 'DeTroyer' | Cultivar 'Angela' |
| Young shoot | anthocyanin coloration absent in the sheath | with anthocyanin coloration present in the sheath |
| Leaf | thicker and rounder than 'Elisabeth' | thinner and more oblong than |

-continued

| | Comparative Varieties | |
|---|---|---|
| Characteristic | Cultivar 'DeTroyer' | Cultivar 'Angela' |
| | | 'Elisabeth' |
| Spathe: main color upper side | approximately RHS 43C, somewhat more orange than 'Elisabeth' | approximately RHS 38 A-B |
| Spadix | shorter and thicker than 'Elisabeth' | longer and thinner than 'Elisabeth' |

I claim:

1. A new and distinct cultivar of *Anthurium* plant named 'Elisabeth,' as illustrated and described.

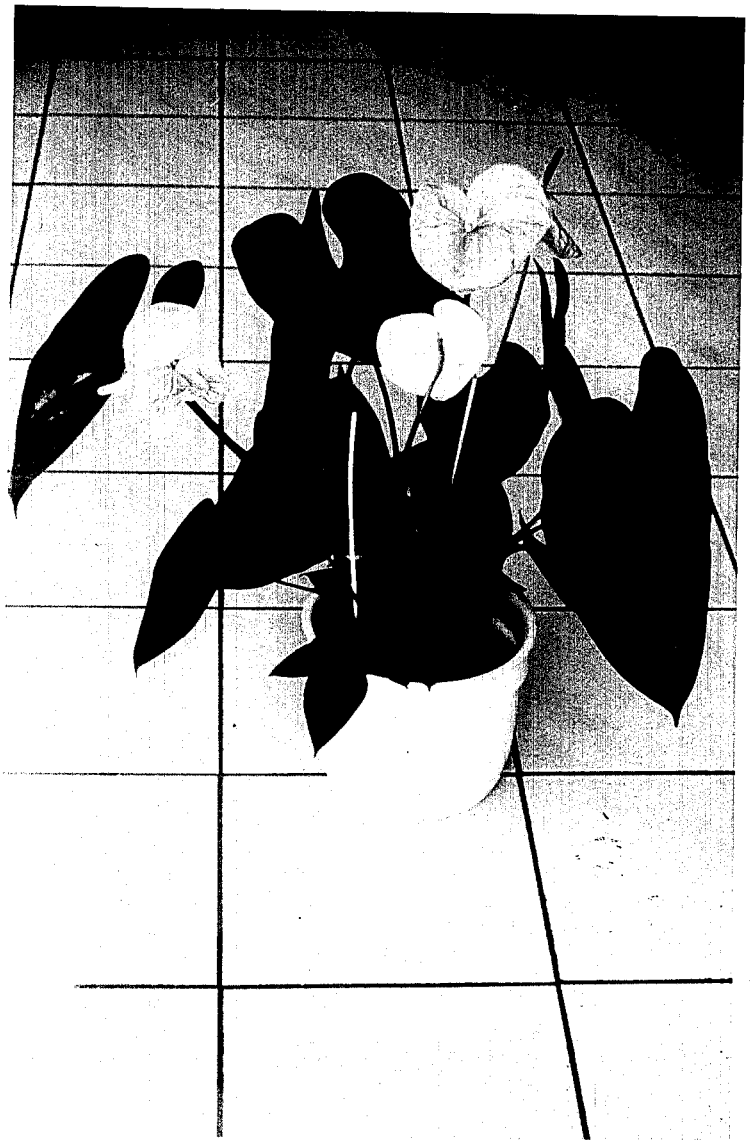

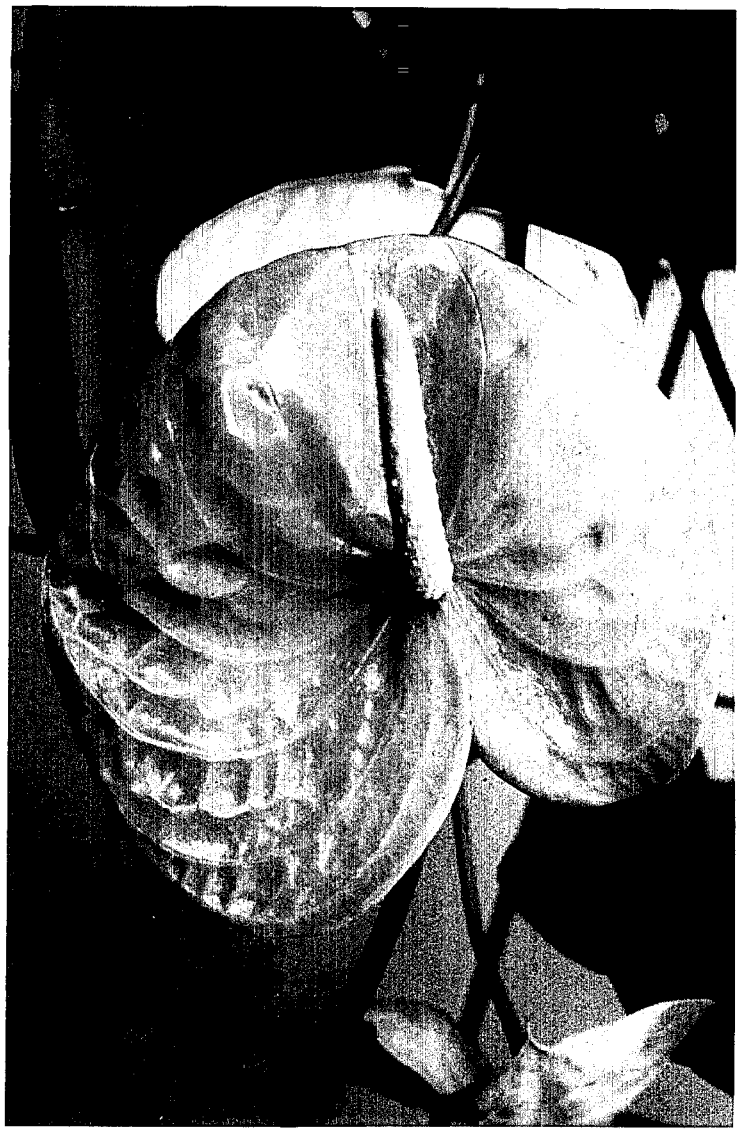

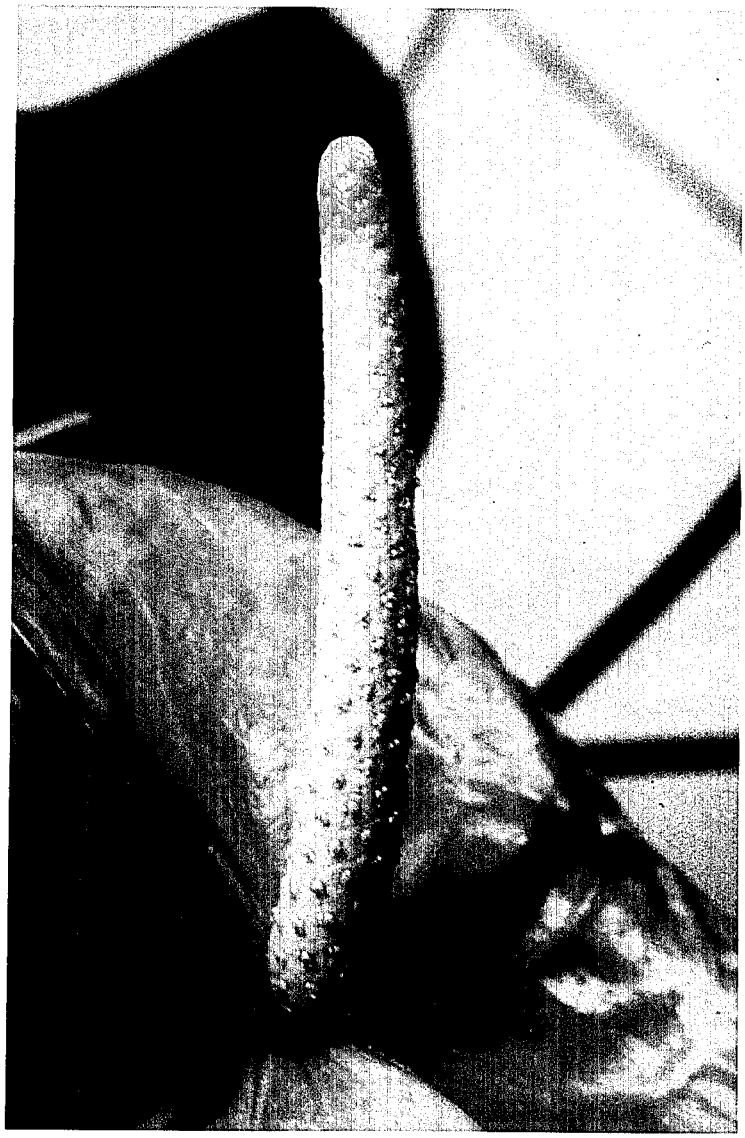

* * * * *